United States Patent [19]

Georgieff

[11] Patent Number: 5,091,369

[45] Date of Patent: Feb. 25, 1992

[54] METHOD OF PROMOTING ENDOGENOUS FAT OXIDATION

[76] Inventor: Michael Georgieff, Gleiwitzerstr.22, 6944-Hemsbach, Fed. Rep. of Germany

[21] Appl. No.: 453,138

[22] Filed: Dec. 12, 1989

Related U.S. Application Data

[63] Continuation of Ser. No. 15,573, Feb. 11, 1987, abandoned, which is a continuation of Ser. No. 707,457, Mar. 1, 1985, abandoned, which is a continuation-in-part of Ser. No. 686,719, Dec. 27, 1984, abandoned.

[51] Int. Cl.$^5$ .............................................. A61K 31/70
[52] U.S. Cl. ....................................... 514/23; 514/724
[58] Field of Search ............................ 514/23, 53, 724

[56] References Cited

PUBLICATIONS

Baessler, *Chemical Abstracts* vol. 67, 1967, Abstract No. 30229g, pp. 2842–2843.
Bassler, *Anaesthesiology and Resuscitation*, 1966 (6), pp. 20–27.
Bassler et al., *Klenische Wochenschrift*, 1965 pp. 169–171.
Baessler, "The Role of Carbohydrates in Parenteral Nutrition", Anesthesiology and Resuscitation, 1966 (6), pp. 20–27.

*Primary Examiner*—Elli Peselev
*Attorney, Agent, or Firm*—Donald Brown

[57] ABSTRACT

A preparation comprising essentially xylitol and glucose in a variable relation, each no more than 200 grams and no less than 20 grams each, as part of total intravenous nutrition support to cover the energy expenditure in humans with reduced ability to utilize amino acids.

1 Claim, No Drawings

METHOD OF PROMOTING ENDOGENOUS FAT OXIDATION

This is a continuation of copending application Ser. No. 07/015,573 filed on Feb. 11, 1987 now abandoned, which is a continuation, of application Ser. No. 707457, filed Mar. 1, 1985, now abandoned, which is a continuation in part of Ser. No. 686,719 filed Dec. 27, 1984, now abandoned.

BACKGROUND

This invention relates to a method of providing total energy requirements of a human who suffers from severe stress or injury, renal disease, liver failure, cancer cachexia or receiving ventilatory support. More specifically, it relates to a carbohydrate mixture e.g., in the form of a solution consisting essentially of glucose and xylitol to cover the energy requirements of a human. The combination of glucose, at a rate no higher than the endogenous glucose production rate between 20 to 200 g/24 hours, with xylitol no higher than maximally 210 g/24 hours, will unexpectedly preserve body protein in humans suffering severe illness, trauma, sepsis, organ failure or other injury, as defined herein, when given in above mentioned combination and dosage.

Currently only solutions containing either glucose, fructose and xylitol, or sorbitol and xylitol are available for the treatment of a human. The major discovery of this invention is that the fructose as well as the sorbitol added to xylitol in any form substantially alternates its specific useful metabolic effects of xylitol during illness, such as enhancing endogenous fat mobilisation and oxidation, enhancing amino acid exchange from peripheral to visceral tissues and thereby increasing the synthesis of secretory proteins like albumin and transferrin.

Fructose, like xylitol is primarily metabolized in the liver (de Kalbermatten N., Ravussin E., Maeder E. et al, Metabolism 29: 62-67, 1980). In the liver cell fructose is activated to fructose-1-phosphate by fructokinase (Zakim D., Hermann R. H., Am J. Clin Nutr. 21: 315-319, 1968), an insulin independent enzyme. The activity of fructokinase though is 5 times higher than all glucose phosphorylating enzymes in the liver (Zakim D, Hermann R. H., Gordon W. C., Biochem Med 2: 427-437, 1969), and 4 times higher than the polyol-dehydrogenase activity (Baessler K. H., Stein G., Belzer W., Biochem Z 346: 171-185, 1966) the initial xylitol degradating enzyme. Fructose-1-phosphate is cleaved by a specific aldolase to two trioses (Zakim D., Hermann R. H., Gordon W. C. Biochem Med 2: 427-437, 1969). In contrast to the aldolase which cleaves fructose-1,6-diphosphate from glucose and xylitol metabolism, the fructose-1-phosphate specific aldolase has a very high activity and is not a rate limiting enzyme (Zakim D., Hermann R. H., Gordon W. C., Biochem Med 2: 427-437, 1969). The rapid initial phosphorylation of fructose and the unlimited cleavage to trioses allows dietary fructose to be metabolized in the Emden-Meyerhof-Pathway in the liver at a far greater rate than glucose and xylitol (Baessler K. H., Stein G., Belzer W. Biochem 2 346: 171-185, 1966). The high turnover rate in the glycolytic pathway during fructose administration therefore increases lactate formation, hepatic fat synthesis. Compared to other carbohydrates like glucose and xylitol, fructose underlies an enhanced conversion to fat in the liver and by increasing the amount of endogenous free fatty acid reesterified to triglycerides in the liver, fructose leads to a damage of the liver during total parenteral nutrition (intravenous feeding). (Forster H., Internist 19: 2-19, 1977). All these metabolic effects can be observed even at low infusion rates ranging from 20-100 g.

Sorbitol is a polyalcohol as xylitol. Sorbitol is also primarily metabolized in the liver (Baessler K. H., Pharm Therap Dent 3: 85-93, 1978) and there dehydrogenated by the same polyol-dehydrogenase as xylitol (Froesch E. R., Zapf J., Keller U., et al, Europ J Clin Invest 2: 627-633, 1978) to fructose. From that step on sorbitol is metabolized like fructose, and can case the same metabolic side effects even at low infusion rates.

Whenever either fructose or sorbitol are added to a solution containing xylitol, the principal metabolic effects of xylitol, moderation of elevated blood glucose and insulin levels, reduction of gluconeogenesis, increase in protein synthesis and enhancement of endogenous as well as exogenous fat oxidation, are attenuated.

Glucose, given above the endogenous production rate of approximately 200 g/24 hours is associated with an increase of blood glucose and insulin levels (Wolfe R. R., Allsop J. R., Burke J. F., Metabolism 28: 210-220, 1979). After injury, glucose given above the endogenous production rate stimulates hepatic lipid synthesis (Wolfe R. R., O'Donell T. F., Stone M. D., Metabolism 29: 892-900, 1980), and reduces endogenous amino acid flux from peripheral to visceral organs (Moldawer L. L., O'Keefe S. J. D., Bothe A., et al, Metabolism 29: 173-180, 1980), thus reducing overall protein synthesis due to restricted amino acid availability. The percentage of infused glucose oxidized, declines when given above the endogenous production rate (Wolfe R. R., Allsop J. R., Burke J. F., Metabolis 28: 210-220, 1979), thus contributing less effective to energy expenditure. In order not to attenuate the metabolic response to severe illness during intravenous feeding with glucose, which is primarily characterised by a mobilisations of the body's own reserves in order to optimize protein synthesis and host defense, glucose should only be given in a dosage under the endogenous production rate ranging from 20-200 g/24 hours (h).

Accordingly it is a goal of this invention to feed the critically ill intravenously so as to moderate blood glucose and insulin elevations and to attenuate the loss of lean body mass by reducing gluconeogenesis and increasing protein synthesis. Current state of the art tries to maintain body protein by stimulating endogenous insulin secretion, or giving it exogenously (Hinton P. Allison S. P., Littlejohn S., Lancet 2: 767-769, 1971), and thereby try to reduce muscle protein breakdown (Woolfson A. M. J., Hertley R. V., Allison S. P. New Engl J Med 300: 14-17, 1979). During the hypoinsulinemic state of traume, xylitol is oxidized at a significantly higher rate than glucose without extensive hyperglycemia (de Kalbermatten N., Ravussin E., Maeder E., et al, Metabolism 29: 62-67, 1980). Xylitol enters the pentose phosphate shunt directly and does not require insulin (Hollman V. S., Reinauer H., Z Ernaehrungswiss 11: 1-7, 1971). Depending on the severity of an injury, the maximal disposal rate of xylitol increases from 0.37 g/kg BWxh in normal to 0.76 g/kg BWxh after injury (Ackerman R. H., Infusionstherapie 7: 113-115, 1980). In contrast to xylitol, maximal glucose disposal rate after injury is reduced by approximately 36%, even supraphysiologic insulin concentrations are not capable of increasing the limit after injury (Blach P. R., Brooks D. C., Bessey P. Q., et al, Ann Surg 196:

420–433, 1982). Therefore any glucose infusion above the endogenous production rate of 200 g during illness will be associated with an increase of blood glucose and insulin levels, causing fatty liver, reduced protein synthesis and inefficient protein preservation. Unlike glucose, intravenously administered xylitol is primarily metabolized in the liver and there converted to glucose independent of insulin, most importantly, xylitol generates the intermediates of glucose metabolism important for amino acid and fat utilisation without having to generate glucose (Pellaton M., Acheson K., Maeder E., et al, JPEN 2: 627–633, 1978).

STATEMENT OF THE INVENTION

The invention described herein is a novel parenteral nutrition solution made essentially from xylitol and glucose, and a method of treatment employing it for use in a human suffering severe stress or injury or significant renal or hepatic disease to reduce nitrogen wasting and its accelerated gluconeogenesis. The novel solution of the invention is comprised of an aqueous xylitol and glucose solution, each no more than 200 g each and no less than 20 g each, suitable for either peripheral (if given at low concentrations) or central venous administration (infusion).

Another aspect of the present invention comprises a method of treatment for a critically ill patient suitable for intravenous purposes to cover the energy expenditure, reduce gluconeogenesis and protein wasting as well as promote endogenous fat oxidation, ketogenesis and amino acid availability for hepatic secretory protein synthesis, leucocytosis and for wound healing.

The invention described herein is based partly upon the recognition that reducing the wasting of tissue protein and gluconeogenesis are critical to effective and successful recovery. In contrast to current state of the art of treating a patient, where protein preservation is tried to be achieved by mainly reducing protein catabolism, this new method preserves body protein by primarily increasing protein synthesis, which is a far more effective way in retaining body protein content. Accordingly, an increased fatty acid oxidation will reduce the obligatory need to catabolize tissue protein for energy and therefore provide more precursors for wound healing, leucocytosis and hepatic secretory protein synthesis, essential for recovery.

Types of humans being beneficially treated herein are for example those having a body nitrogen loss greater than 4 g/day or blood glucose concentration greater than 120 mg/ml.

It should be understood that other nitritional substances may be administered so long as sorbitol or fructose are not included and so long as these substances do not interfere with the usefulness of the composition of the invention.

The following examples further describe the invention.

A sterile, nonpyrogenic, stable solution suitable for intravenously infusion into a peripheral or central vein of critically ill trumatized patients is prepared from pure anhydrous glucose and anhydrous xylitol, which are dissolved in distilled water in the following concentrations.

|  | GLUCOSE | XYLITOL |
| --- | --- | --- |
| grams/liter | 20 to 200 g | 20 to 200 g |

Sterilization is carried out in a convention manner. In the foregoing formula, the ratio of glucose to xylitol is variable, but the concentration of each energy source should be no higher than maximally 200 g each.

As used in this application, glucose is used in its ordinary sense as the active D-glucose.

What is claimed is:

1. A method of promoting endogenous fat oxidation in a human in need thereof comprising administering through a vein of said human patient, a composition consisting essentially of 200 grams/liter of D-xylitol and 200 grams/liter of glucose.

* * * * *